United States Patent
Gentry et al.

(10) Patent No.: US 8,030,627 B2
(45) Date of Patent: Oct. 4, 2011

(54) TREATMENT PLANNING TOOL FOR HEAVY-ION THERAPY

(75) Inventors: John Roy Gentry, Gastonia, NC (US); Raymond Terry Riddle, Middleton, WI (US); Neal Robert Miller, Waunakee, WI (US)

(73) Assignee: Standard Imaging Inc., Middleton, WI (US)

( * ) Notice: Subject to any disclaimer, the term of this patent is extended or adjusted under 35 U.S.C. 154(b) by 347 days.

(21) Appl. No.: 12/271,594

(22) Filed: Nov. 14, 2008

(65) Prior Publication Data

US 2009/0134345 A1    May 28, 2009

Related U.S. Application Data

(60) Provisional application No. 60/990,121, filed on Nov. 26, 2007.

(51) Int. Cl.
*A61N 5/10* (2006.01)

(52) U.S. Cl. .................................................. 250/492.3
(58) Field of Classification Search ................. 250/492.3
See application file for complete search history.

(56) References Cited

U.S. PATENT DOCUMENTS

| 7,202,486 B2 * | 4/2007 | Gentry et al. .............. 250/492.3 |
| 2007/0145916 A1 | 6/2007 | Caporaso et al. |
| 2009/0008575 A1 * | 1/2009 | Okazaki et al. ............ 250/492.1 |

OTHER PUBLICATIONS

Bortfeld et al, "An analytical approximation of depth-dose distributions for therapeutic proton beams", Physics in Medicine and Biology, vol. 41 (1996), pp. 1331-1339.*

* cited by examiner

*Primary Examiner* — Jack Berman
(74) *Attorney, Agent, or Firm* — Boyle Fredrickson, S.C.

(57) ABSTRACT

A dose calculator for heavy-ion therapy systems uses a limited number of spread out Bragg peak models obtainable by a particular therapy system, the models which may be adjusted in energy (offset) and dose contribution (treatment time) to produce a unique composite dose having a complex dose profile with limited reduced time.

20 Claims, 3 Drawing Sheets

TREATMENT PLANNING TOOL FOR HEAVY-ION THERAPY

CROSS REFERENCE TO RELATED APPLICATIONS

This application claims the benefit of U.S. Provisional application 60/990,121 filed Nov. 26, 2007 and hereby incorporated by reference.

BACKGROUND OF THE INVENTION

The present invention relates to heavy-ion therapy systems for the treatment of cancer and the like, and in particular to a treatment planning tool for generating settings for particular dose profiles for heavy-ion beams.

External beam radiation therapy may treat a tumor within a patient by directing high-energy radiation in one or more beams toward the tumor. The radiation commonly may be photons, such as x-rays or electrons.

Standard electron beam and photon devices are often used to provide single energy beams during treatment. More complex dose patterns can be obtained, however, with combinations of beams of multiple radiation energy. U.S. Pat. No. 7,202,486 to Gentry et al. issued Apr. 10, 2007, entitled: Treatment Planning Tool For Multi-Energy Electron Beam Radiotherapy, assigned to the same assignee as the present invention and hereby incorporated by reference, describes a tool allowing a physician to combine multiple electron beam energies or combined electron/photon energies available on a standard, single beam radiotherapy system. The tool, which may operate on a stand-alone desktop computer, accepts a simple characterization of a desired beam depth dose profile and produces a treatment plan using multiple energies and that can be entered into a radiation therapy treatment planning system and implemented using successive exposures from the radiation therapy machine. The use of multiple energy beams allows for better dose conformance to a treatment zone.

Recent interest has developed in the use of protons or other heavy-ions for external beam therapy. Unlike electrons and x-rays, protons may be given sufficient energy to penetrate an arbitrary amount of tissue and then to stop within the tissue, eliminating exit dose through healthy tissue on the far side of a tumor. Further, the dose deposited by a proton beam is not uniform along the entrance path of the beam, but rises substantially at a "Bragg peak" near a point where a proton stops within the tissue. These two features allow improved concentration of dose within the tumor.

A mono-energetic beam of protons produces a narrow Bragg peak whose range (depth in the tissue) can be controlled by controlling the energy or acceleration of the protons. In theory, an arbitrary dose profile can be produced using a mono-energetic beam of protons by moving the beam in energy range and angle to dimensions to sequentially "paint" a treatment zone. By changing a dwell time of the proton beam at a particular location, an arbitrary dose profile may be produced.

Current proton therapy may alternatively use a "spread out Bragg peak" (SOBP) employing a poly-energetic proton beam having multiple Bragg peaks extending over a range of depths to produce a plateau of roughly constant dose. This approach accommodates poly-energetic proton sources and greatly simplifies the mechanics of treatment by allowing an entire tumor area, embraced by the plateau, to be treated simultaneously without complex movement of the beam.

Producing a spread out Bragg peak may be done, for example, by passing a mono-energetic or narrow poly-energetic beam of protons through a rotating wedge "propeller" that modulates the energy of the proton beam with constantly changing variable thickness of material or through a grid having varying thicknesses within the cross-section of the beam. The overall energy of the beam, and hence the center of the plateau may be adjusted in range or depth by using a bolus or movable wedge to center the spread out Bragg peak at the tumor.

Treatment planning using an SOBP beam simply requires adjusting the width of the plateau of the SOBP to cover the tumor and centering the range of the plateau on the tumor, and then applying the proton beam for a desired period of time to achieve a uniform tumor dose.

SUMMARY OF THE INVENTION

The present inventors have recognized that the approach of using an SOBP beam for treatment does not require a uniform dose to be applied to the area of the beam but that multiple successive applications of different SOBP beam profiles can be used to create more complex dose distributions. The present invention provides a tool for combining SOBP beams to realize more sophisticated treatments without the need for the complexity of equipment or planning required when using a mono-energetic beam.

Specifically then the present invention provides a treatment planning tool for use with a heavy-ion therapy machine producing a spread out Bragg peak (SOBP) beam where the treatment tool models one or more predefined SOBP dose profiles for a range of energies and treatment times, and mathematically combines the models of the SOBP dose profiles with different energies and/or treatment times to define a treatment profile that is not obtainable with one model at any given energy and treatment time. Identification of the models, the energies, and treatment times for implementation are output and used for sequential exposures on the heavy-ion therapy machine.

It is thus a feature of at least one embodiment of the invention to provide a middle ground between the alternatives of many exposures with mono-energetic proton beams and single exposures with flat profile SOBP beams. It is another feature of at least one embodiment of the invention to provide a system that may work effectively with a limited number of verified machine settings by providing models of those verified settings and combining those models. It is a further feature of at least one embodiment of the invention to provide an improved SOBP treatment protocol providing less abrupt distal treatment edges for better immunity to patient motion.

The models may employ the form:

$$D_{SOBP}(d) = \frac{D_0}{1 + k\left(\frac{d_a - d}{d_b - d_a}\right)^p}$$

where:
$d_a$ is a distance along the beam of a proximal edge of an SOBP plateau;
$d_b$ is a distance along the beam of a distal edge of an SOBP plateau; and
$D_0$ is a predefined normal dose value for a given treatment.

It is thus another feature of at least one embodiment of the invention to provide an analytic form for a spread out Bragg peak that may be applied to empirical measurements of machine performance (without knowledge of the underlying proton energy distributions) and that may be readily summed to produce a composite dose per the present invention.

In this model, k may be substantially 0.44 and p may be substantially 0.6.

It is thus a feature of at least one embodiment of the invention to provide a model suitable for protons in watery tissue.

The program may further output a graph of a depth-dose profile of combined sequential proton exposures and may also show a plot of a depth-dose profile of each constituent sequential proton exposure in isolation.

It is thus a feature of at least one embodiment of the invention to provide a simple display allowing verification by a physician and/or interactive adjustment of the constituent beams.

The program may further accept input from a user to select particular ones of the models, energy, and dose of the combined models.

It is thus a feature of at least one embodiment of the invention to allow manual combination of models and hence beams.

The program may accept a conformance limit defining a maximum variation in dose between the treatment profile of the composite beam and a desired dose over a depth range.

It is thus a feature of at least one embodiment of the invention to permit automatic construction of desired doses out of multiple models by providing a quantitative endpoint.

The models may be prepared by taking measurements on an ion-therapy machine at different settings and fitting them to mathematical functions or by entering pre-defined standardized data from the ion-therapy machine, i.e. "gold data". Different models may be provided for each energy-spreading element of a heavy-ion therapy machine, for example.

Thus it is a feature of at least one embodiment of the invention to provide a system that may greatly simplify treatment planning by providing a range of dose profiles from a smaller number of relatively simple and well-characterized dose profiles.

These particular objects and advantages may apply to only some embodiments falling within the claims and thus do not define the scope of the invention.

DETAILED DESCRIPTION OF THE INVENTION

Figure 1:
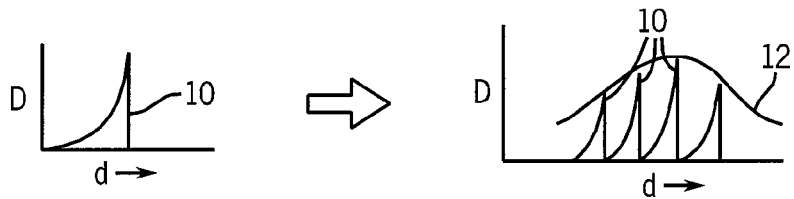
FIG. 1 is a graph of dose vs. distance for a mono-energetic proton beam showing a resultant narrow Bragg peak that may be used to produce a complex dose profile to a tumor over many exposures.

Referring now to FIG. 1, a mono-energetic beam of protons provides a dose profile 10 indicating energy deposition by a mono-energetic beam of protons as a function of distance into normal tissue. For such a mono-energetic beam, the dose profile 10 will be a relatively sharp Bragg peak as is understood in art. By changing the energy of the mono-energetic beam, multiple such Bragg peaks 10' may be produced at different distances or ranges in the tissue and, by controlling the flux of the beam or changing of the dwell time of the beams at each range, an arbitrary dose profile 12 may be created.

Increased treatment speed and simplicity of treatment planning and construction of the heavy-ion therapy machine may be provided by using a poly-energetic proton beam producing a spread out Bragg peak 14 having a plateau region 16 of substantially constant dose. The range of energies of protons within the beam may apply a substantially uniform dose profile 12 to a treatment area.

Figure 2:
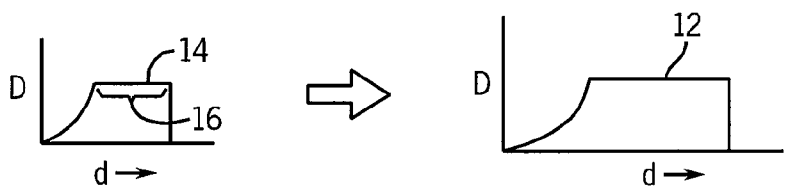
FIG. 2 is a graph similar to that of FIG. 1 for a weighted poly-energetic proton beam showing a spread out Bragg peak (SOBP) that may be used to deposit a uniform dose to a tumor with a single exposure.
Figure 3:
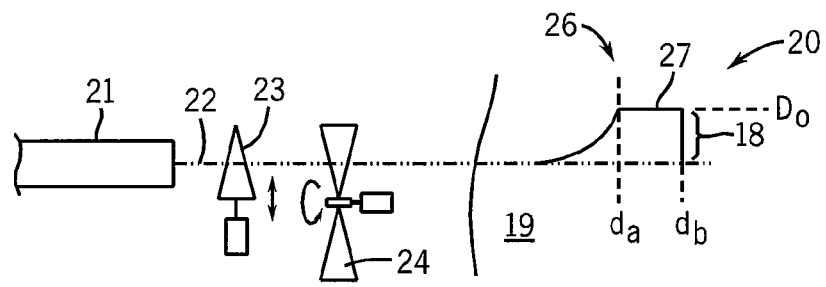
FIG. 3 is a simplified cross-sectional representation of a standard heavy-ion therapy system using a propeller system to produce a spread out Bragg peak.

Referring now to FIG. 3, a heavy-ion therapy machine 20 for producing a spread out Bragg peak per FIG. 2 may provide for a proton source 21 providing a proton beam 22 having a substantially uniform cross-section and area. Currently, such proton sources are particle accelerators such as synchrotron, cyclotron, or the like, but may include dielectric wall particle accelerators (DWPA) in the future. The proton beam 22 may pass through a range shifter 23, for example, a movable wedge inserting a predetermined known thickness of material into the proton beam 22 to control its average energy $E_0$ and hence range, roughly according to the equation:

$$R(E) = \alpha E_0^p \quad (1)$$

where R is the range of the center of the Bragg peak and E0 is the center energy of the poly-energetic beam. The value of p is approximately 1.8 for protons with energies between 10 and 200 Mev. ⬚ is approximately 1.9×10−3 for protons in water.

The energy adjusted proton beam 22 may be received by a range spreader 24, for example, a propeller of material rotating to rapidly vary a thickness of material inserted in the beam 22 thereby producing a varying energy of the beam 22 and, in turn, effectively spreading the length of the plateau of the SOBP as will be described. Range shifter 23 and range spreader 24 both vary the energy of the beam 22; however, range shifter 23 operates more slowly and may for example be maintained in a constant position determined by an operator during an exposure, while the range spreader 24 is in constant rotary motion during an exposure, sweeping through energy ranges at a much higher rate than the range shifter 23.

The beam 22 may be received by a patient 19 to deposit energy in patient tissue according to a SOBP model 26. Generally the SOBP model 26 will have a substantially constant plateau 27 defined with a width defined by a proximal edge at a depth da and a distal edge at a depth db and a height 28 determined by the total flux of protons during the exposure time.

The center of the plateau 27 will be determined by the range shifter 23 while the length of the plateau 27 will be determined by the range spreader 24. Several different range spreaders 24 may be used to provide for different lengths of plateau 27 in the SOBP, for example, by replacing the propeller with one having different variations in material thickness or by changing the radius at which the beam 22 intersects the propeller for propellers whose thickness varies both circumferentially and radially. Other mechanisms may be used for range spreading, for example gratings having triangular grooves ruled in their surface to provide a statically variable width material. Spreading foils may be used to change the cross-sectional area of the beam 22 which will generally have a Gaussian profile.

Figure 4:
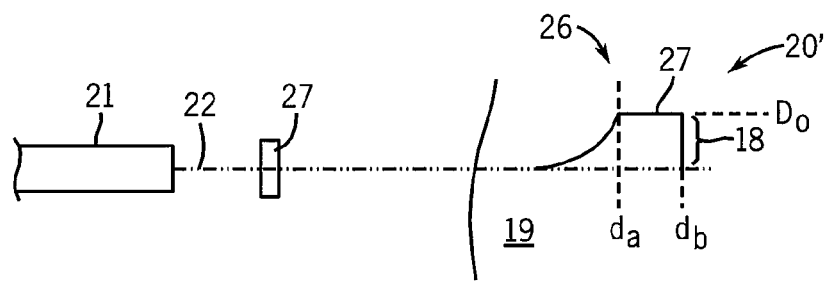
FIG. 4 is a figure similar to that of FIG. 3 showing a dielectric wall accelerator based heavy-ion therapy system providing a spread out Bragg peak.

Referring now to FIG. 4, in an alternative embodiment, the heavy-ion therapy machine 20' may have a proton source 21 that is a dielectric wall particle accelerator (DWPA) such as is described in U.S. Patent Application 20070145916 to Caporaso et al. published Jun. 28, 2007 and entitled: "Sequentially Pulsed Traveling Wave Accelerator Producing Directly A Mono-Energetic Or Narrowly Poly-Energetic Proton Beam". The DWPA may directly produce a mono-energetic or narrowly poly-energetic proton beam 22. This beam 22 may be received by a range shifter 23 or range spreader 24 or these functions may be implemented electronically by control of the acceleration provided by the DWPA possibly with a filter/spreader 25 adjusting the weighting of a beam of energy swept protons. This embodiment may also be used to generate a SOBP model 26 with a substantially flat plateau 27 for ease of planning and treatment. The filter spreader may provide a weighting to different energies of protons to produce the flat plateau 27 of the SOBP model 26. This SOBP model 26 may be desired even if a mono-energetic beam is possible either for simplicity of treatment planning or to simplify the validation of the beam strength as may be done easily for a limited number of settings.

Figure 7:
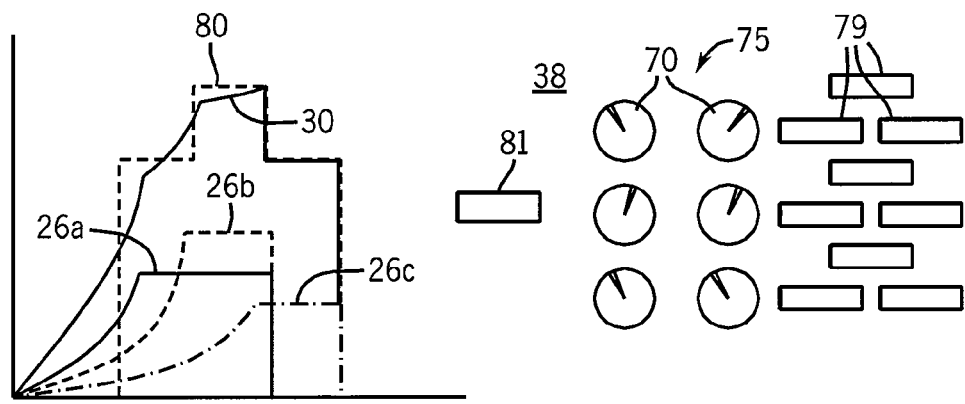
FIG. 7 is a graphical display on the computer of FIG. 5 showing the combination of modeled SOBP models and manual controls to manipulate those models that may be implemented by the program of FIG. 6 for production of a complex dose profile.

Referring now to FIG. 7, the present invention allows SOBP models 26 to be combined to produce a more complex composite dose profile 30, for example, having, in this example, greater dose (indicated by the height of the composite dose profile 30) at the center of a treatment region and a less abrupt distal edge to accommodate location error caused by patient motion or the like. The present invention aids in generating this complex composite dose profile 30 by permitting a summation of several SOBP models 26a, 26b, and 26c, each achievable with a different setting of the heavy-ion therapy machine 20. Together, sequential exposures of the patient 19 with these settings will produce the complex composite dose profile 30.

Figure 5:
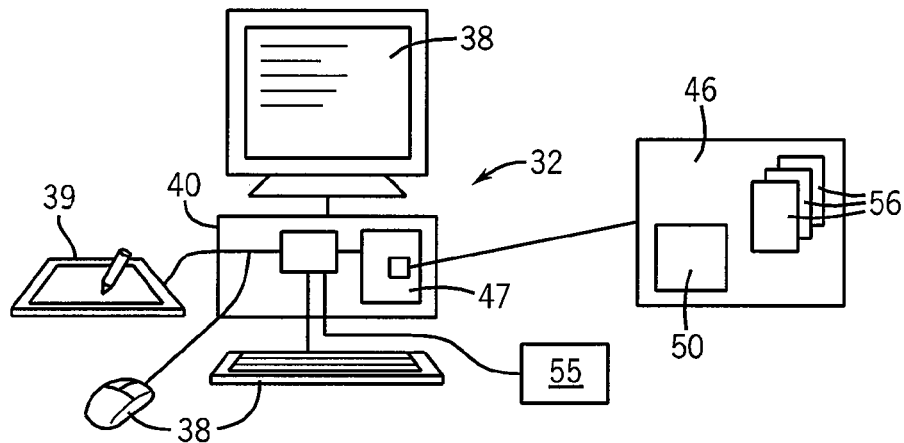
FIG. 5 is a block diagram of a standard desktop computer system suitable for implementing the present invention as a program.

Referring now also to FIG. 5, the present invention is preferably implemented as a software tool to generate settings for a heavy-ion therapy machine 20 or 20' that will produce a composite dose profile 30 matching a user-entered desired dose 80. In the preferred embodiment, software 46 (including both a program and data structures) is executed on a standard desktop computer system 32 having a graphic display screen 36 that may display the representation of FIG. 7 and a data entry device 38 such as a keyboard and trackball or mouse, and having a graphics tablet 39, scanner, light pen, touch screen or other drawing input device for accepting hand-drawn inputs such as the desired dose 80. The terminal 34 may communicate with a processor unit 40 including a processor 44 and memory 47, the latter holding the software 46 including data files 56 and modeling program 50 reading the data files 56 and executing the method of the present invention.

The processor unit 40 may provide for a connection to an external device 55 to receive the data generated by the invention. The external device 55 may be as simple as a printer or may be control electronics for heavy-ion therapy machine 20 or 20'. The computer system 32 need not have direct electrical connection to the heavy-ion therapy machine 20 or 20' of FIGS. 3 and 4, but the latter may instead receive data manually entered by an operator based on output from the present invention.

Figure 6:
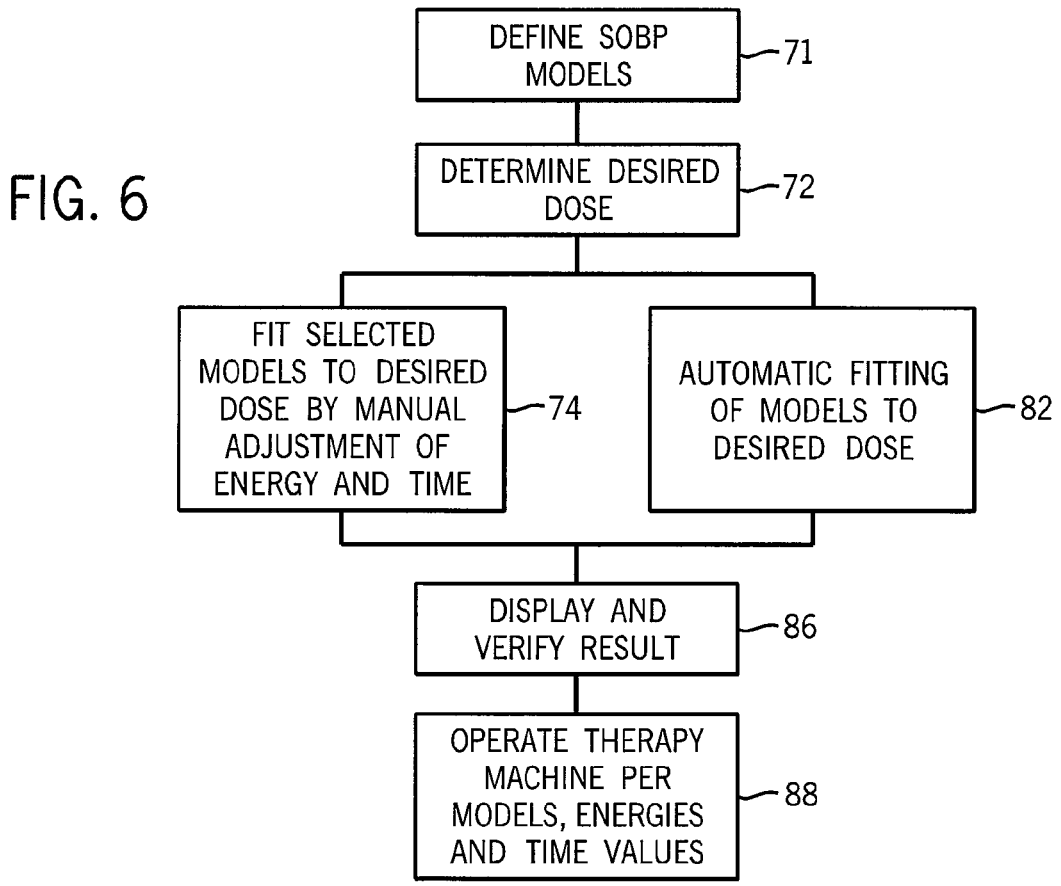
FIG. 6 is a flow chart showing the steps of the execution of the program of FIG. 5 implementing the present invention.

Referring now to FIG. 6, the method of the present invention starts with the collection of SOBP files 56 as indicated by process block 71. As noted above, these SOBP files 56 hold normalized depth dose data for each SOBP model 26 taken along the central axis of the heavy-ion therapy machine 20 or 20' for different settings. Generally for heavy-ion therapy machine 20, a single SOBP model 26 will be obtained for each setting of the range spreaders 24 but one SOBP model 26 can be used and mathematically modified for different settings of the range shifter 23. Alternatively, multiple profiles can be obtained for each particular setting of the range spreaders 24 and for various different settings of the range shifter 23. For the heavy-ion therapy machine 20', a single SOBP model 26 will be obtained for each filter/spreader 25 and possibly for different energy settings of the proton source 21. Not all settings need to be modeled if a composite dose profile 30 can be adequately formed from a limited number of SOBP models 26.

These SOBP models 26 can be expressed and stored as data points describing the curves shown in FIG. 7 and thus serve as a numerical model for the behavior of the heavy-ion therapy machine 20 or 20'. Alternatively, if the SOBP models 26 have a substantially flat plateau 27, the data may be approximated with an analytical model according to the following equation described in: "An Analytical Approximation Of Depth-Dose Distributions For Therapeutic Proton Beams" Bortfeld et al, Phys. Med. Biol. 41 (1996) 1331-1339:

$$D_{SOBP}(d) = \frac{D_0}{1 + k\left(\frac{d_a - d}{d_b - d_a}\right)^p} \quad (2)$$

where:
$d_a$ is a distance along the beam of a proximal edge of an SOBP plateau;
$d_b$ is a distance along the beam of a distal edge of an SOBP plateau
$D_0$ is a predefined normal dose value for a given treatment;
k is substantially 0.44; and
p is substantially 0.6.

This equation provides a reasonably accurate description of a spread out Bragg peak to within plus or ±1.5% of D0 so long as the quantity $$\left(\frac{d_a - d}{d_b - d_a}\right)$$

is less than 10.

Using this analytical model, less data need be stored and the mathematical combination of different SOBP models 26 is greatly simplified. Another advantage of an analytic approach is that the SOBP models 26 may be easily extracted from actual measurements on a heavy-ion therapy machine 20 or 20' by measuring distal and proximal edges of the profile of an actual beam together with the dose height 18.

Generally the SOBP model 26 may be normalized to a standard dose value for a fixed period of time, for example, one second, allowing new SOBP models 26 to be created simply by multiplying the values of the SOBP model 26 by either number of seconds of exposure or the like. In addition each SOBP model 26 may be normalized to a standard center energy value E0 so that SOBP models 26 shifted in range may be readily generated using equation (1).

The SOBP models 26 may be computed or measured for particular types of heavy-ion therapy machines 20 and 20' and placed in different files 56 that may be selected among depending on the type of heavy-ion therapy machine 20, 20' employed. Each SOBP model 26 may be identified to the particular settings (e.g. setting of range shifter 23, range spreader 24 or filter/spreader 25) so as to be readily identifiable. In addition, the particular heavy-ion therapy machine 20, 20' to which the modeled SOBP model 26 relates (e.g., manufacturer and model number) may be included in this identification of file 56 for use in facilities with multiple machines.

After the collection of the SOBP models 26a-c, a proton treatment plan may be determined. As indicated by process block 72, at the beginning of the treatment process, the user is prompted to enter a description of a desired dose 80. Referring again also to FIG. 5, this description can be entered by drawing the desired dose 80 using the tablet 39 or other device, and this drawing is digitized for display on the screen 36. At this time a dose conformance limit may be entered indicating how closely to this desired dose 80 the composite dose profile 30 should conform.

Referring now to FIGS. 6 and 7, at process block 74 all or selected SOBP models 26a-c may be displayed on the screen 36 at arbitrary energy and dose levels. The user may select the particular SOBP models 26 to use in forming the composite dose profile 30. For this purpose, the screen may provide for user controls 75, for example, a pair of controls 70, for example virtual knobs, associated with each of the SOBP models 26a-26c. These controls 70 allow adjustment of the energy E0 (range) and treatment time to be assigned to each of the SOBP models 26a-26c in producing the composite dose profile 30. Values for energy, treatment time and model identification are provided in corresponding text boxes 79 that change as the controls 70 are changed. A color-coding also may be used to associate controls 70 with particular curves of SOBP models 26a-26c.

As the controls 70 are moved, a particular SOBP model 26 plateau 27 will move left and right (with energy) according to equation (1) widening and shrinking slightly. As the controls 70 are moved, the height of the plateau 27 will move up or down with respect to changes in treatment time for the particular associated SOBP model 26. A plot of the changing SOBP model 26 may be generated from energy calculated points da and db and the normalized dose from equation (2) described above.

During this process, the selected SOBP models 26a-26c will be summed to produce a composite dose profile 30 which is plotted so that it can be conformed to the desired dose 80 also visible on the screen 36. A quantitative conformance value 81, for example integrating the error between the composite dose profile 30 and desired dose 80 may also be displayed. In this way, an individual may fit existing SOBP models 26a-26c representing achievable beams from the heavy-ion therapy machine 20 or 20' to the desired dose 80.

Alternatively, as indicated by process block 82 this matching may be automated through the use of a number of well-known algorithms, including for example a greedy algorithm starting with the SOBP model 26 having the largest plateau width 17 (greatest range spreading) that will fit within the dose profile 16' which is adjusted in range and dose iteratively to fit appropriately with the desired dose 80, then moving down the SOBP model 26 with respect to widths 17 to fit the difference between the desired dose 80 and the dose achieved so far. This approach may be rendered possible with normalized SOBP models 26 because of the great flexibility in shifting range and height of the normalized SOBP models 26. In this process, the user may select the particular SOBPs models 26 to be used for the automated fitting process, and the number of different treatments (or SOBP models) that will be employed.

Multiple different combinations of SOBP models 26 may be generated and presented to the user for selection upon completion of the automatic fitting process. Each solution may indicate how closely it conforms to the entered dose profile 16' with a display of a quantitative conformance value 81 (not shown). Each composite dose profile 30 may be a different color and presented with a corresponding number that may be entered into the data entry device 38 to select that composite dose profile 30. In the event that there is no solution within a pre-determined conformity limit, the user is informed of such and prompted to consider relaxing the conformity limit or to generate a different composite dose profile 30.

If a solution is obtained either through block 74 or block 82 it is output at process block 86 for verification by the user. This verification process may include for example displaying the statistics indicating the conformity of desired dose 80 to composite dose profile 30 as well as the data provided by text box 79.

As indicated by process block 88, the data describing the particular SOBP models 26 and their energy and treatment times may then be entered as settings on a heavy-ion therapy machine 20 or 20' and used to select range shifting per range shifter 23, and energy spreading per range spreader 24 or filter/spreader 25, or this information may be provided directly to the heavy-ion therapy machine 20 or 20' for automatic implementation.

Figure 8:
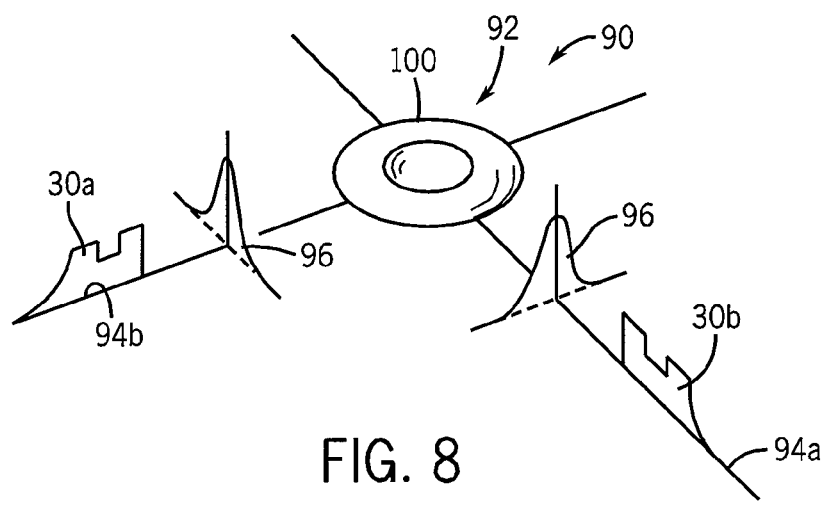
FIG. 8 is a simplified perspective representation of treatment planning using the present invention along two beam axes.

Referring now to FIG. 8, in an alternative embodiment the present invention may be incorporated into a treatment planning system 90 providing dose planning for treatments made along multiple axes 94a and 94b. The treatment planning system 90 may also be executable on the processor unit 40 and may use the calculated total composite dose profiles 30a and 30b (along the different axes 90a and 90b to compute a dose applied to a particular region 92). In this case, the composite dose profile 30 will also include a cross-sectional profile 96 being generally a Gaussian distribution determined by the collimation of a proton beams. This information may be used to develop a two or three-dimensional dose profile 100 indicating the combination of dose deposited along with two different axes 94a and 94b. Additional axes may also be incorporated into a complex treatment planning system 90.

It will be understood that the present invention does not require the use of SOBP models 26 with flat plateaus 27 but may use beams modeled to have, for example, a declining plateau for better summation properties. In addition, the present invention may be used to provide modeling of electrons or photons in addition to the SOBP models for hybrid treatments.

It should be understood that the invention is not limited in its application to the details of construction and arrangements of the components set forth herein. The invention is capable of other embodiments and of being practiced or carried out in various ways. Variations and modifications of the foregoing are within the scope of the present invention. It also being understood that the invention disclosed and defined herein extends to all alternative combinations of two or more of the individual features mentioned or evident from the text and/or drawings. All of these different combinations constitute various alternative aspects of the present invention. The embodi-

We claim:

1. A treatment planning tool for use with a heavy-ion therapy machine producing a spread out Bragg peak (SOBP) heavy-ion beam, the treatment planning tool comprising a program embodied in a non-transitory computer-readable medium, the program executing on a computer to:
   (a) model one or more predefined SOBP dose profiles for a range of energies and treatment times of heavy-ions;
   (b) receive input from a user describing a desired treatment;
   (c) mathematically combine the models of the SOBP dose profiles with different energies and/or treatment times according to the user input to define a treatment profile that is not obtainable with one model at any given energy and treatment time; and
   (d) output data indicating the models, the energies, and treatment times for implementation as sequential exposures on the heavy-ion therapy machine.

2. The treatment planning tool of claim 1 wherein the models employ a form:

$$D_{SOBP}(d) = \frac{D_0}{1 + k\left(\frac{d_a - d}{d_b - d_a}\right)^p}$$

where:
   $d_a$ is a distance along the beam of a proximal edge of an SOBP plateau;
   $d_b$ is a distance along the beam of a distal edge of an SOBP plateau; and
   $D_0$ is a predefined normal dose value for a given treatment.

3. The treatment planning tool of claim 2 wherein the heavy-ions are protons and:
   k is substantially 0.44; and
   p is substantially 0.6.

4. The treatment planning tool of claim 1 wherein the program further displays a graph showing a plot of a desired depth-dose profile of a combined sequential heavy-ion beam exposure.

5. The treatment planning tool of claim 4 wherein the program further receives the desired depth-dose profile from a drawing or graphing input device.

6. The treatment planning tool of claim 4 wherein the graph also shows a plot of a depth-dose profile of each constituent sequential exposure in isolation.

7. The treatment planning tool of claim 6 wherein the program further accepts input from the user to select a subset of the models and energy and dose of the selected models.

8. The treatment-planning tool of claim 1 further accepting input from the user describing a desired dose and a conformance limit defining a maximum variation between the treatment profile and the desired dose over a depth range.

9. The treatment planning tool of claim 1 wherein the program further accepts multiple files each providing one or more models associated with a particular heavy-ion beam therapy machine.

10. The treatment-planning tool of claim 1 further including a treatment-planning program wherein the treatment planning program models a dose produced by the sequential exposures.

11. The treatment planning tool of claim 10 wherein the treatment planning program models a dose over three dimensions using the output data along applied multiple one treatment axes.

12. A method of heavy-ion therapy comprising the steps of:
   (a) preparing mathematical models of multiple predefined SOBP models for a range of energies and treatment times of heavy-ions for a particular heavy-ion therapy machine;
   (b) receiving input data from a user describing a desired treatment,
   (c) mathematically combining the models of the SOBP dose profiles on an electronic computer executing a stored program, the models modified by energies and/or treatment times according to the user input, the combining to define a treatment profile that is not obtainable with one model at any given energy and treatment time; and
   (d) operating the heavy-ion therapy machine using the models, the energies, and treatment times of step (c) in sequential exposures.

13. The method of claim 12 wherein the models are prepared by a method selected from the group consisting of: taking measurements made on the heavy-ion therapy machine at different settings and entering pre-defined standardized data from a predefined standard ion-therapy machine and then fitting them to mathematical functions.

14. The method of claim 12 wherein the heavy-ion therapy machine provides different energy spreading elements and wherein the models include different models for each energy spreading element.

15. The method of claim 12 wherein the heavy-ions are protons and the models employ a form:

$$D_{SOBP}(d) = \frac{D_0}{1 + k\left(\frac{d_a - d}{d_b - d_a}\right)^p}$$

where:
   $d_a$ is a distance along the beam of a proximal edge of an SOBP plateau;
   $d_b$ is a distance along the beam of a distal edge of an SOBP plateau
   $D_0$ is a predefined normal dose value for a given treatment;
   k is substantially 0.44; and
   p is substantially 0.6.

16. The method of claim 12 including the step of displaying a graph showing a plot of a desired depth-dose profile of a combined sequential exposure.

17. The method of claim 16 including the step of receiving the desired depth-dose profile from a drawing input device allowing hand drawing of the desired depth-dose profile.

18. The method of claim 17 wherein the graph also shows a plot of a depth-dose profile of each constituent sequential exposure in isolation.

19. The method of claim 12 including the step of accepting input from the user to select one of the models, energy, and dose of the combined models.

20. The method of claim 12 including the step of generating multiple files each providing one or more models associated with a particular heavy-ion therapy machine.

* * * * *